United States Patent
Zhou et al.

(10) Patent No.: US 12,378,279 B2
(45) Date of Patent: Aug. 5, 2025

(54) NICOTINAMIDE RIBOSIDE HYDROGEN MALATE CRYSTAL, AND ITS PREPARATION METHOD AND APPLICATION

(71) Applicant: Bonte Biological Engineering (Shenzhen) Co., Ltd., Shenzhen (CN)

(72) Inventors: Zhigang Zhou, Shenzhen (CN); Taixian Wen, Shenzhen (CN); Jihai Huang, Shenzhen (CN)

(73) Assignee: Bonte Biological Engineering (Shenzhen) Co., Ltd., Shenzhen (CN)

( * ) Notice: Subject to any disclaimer, the term of this patent is extended or adjusted under 35 U.S.C. 154(b) by 0 days.

(21) Appl. No.: 19/031,698

(22) Filed: Jan. 18, 2025

(65) Prior Publication Data
US 2025/0163094 A1   May 22, 2025

(30) Foreign Application Priority Data
Jul. 3, 2024  (CN) .......................... 202410881394.X

(51) Int. Cl.
*C07H 19/048* (2006.01)
*C07C 59/245* (2006.01)

(52) U.S. Cl.
CPC ......... *C07H 19/048* (2013.01); *C07C 59/245* (2013.01)

(58) Field of Classification Search
None
See application file for complete search history.

(56) References Cited

U.S. PATENT DOCUMENTS

2022/0135610 A1\*   5/2022   Schabert .............. C07H 19/048
536/28.1

FOREIGN PATENT DOCUMENTS

| CN | 107428791 A | 12/2017 |
|---|---|---|
| CN | 111454311 A | 7/2020 |
| CN | 111848710 A | 10/2020 |
| CN | 113563502 A | 10/2021 |
| CN | 114423771 A | 4/2022 |

\* cited by examiner

*Primary Examiner* — Layla D Berry

(57) ABSTRACT

A nicotinamide riboside hydrogen malate crystal has characteristic peaks respectively at $2\theta$ values of 3.1703±0.2, 6.6434±0.2, 12.5953±0.2, 14.7209±0.2, 15.8502±0.2, 16.5144±0.2, 17.0509±0.2, 17.7053±0.2, 18.6569±0.2, 18.9470±0.2, 19.7757±0.2, 21.4535±0.2, 21.9161±0.2, 22.3721±0.2, 22.9562±0.2, 24.0469±0.2, 24.8641±0.2, 25.2183±0.2, 25.7679±0.2, 27.2584±0.2, 28.5494±0.2, 36.5968±0.2 and 36.8355±0.2. In the preparation of such crystal, DL-malic acid is dissolved in a solvent under stirring, to which a nicotinamide riboside chloride and a base are added for reaction. The reaction mixture is cooled, crystallized at a constant temperature, filtered and dried to give the desired crystal.

5 Claims, 7 Drawing Sheets

NICOTINAMIDE RIBOSIDE HYDROGEN MALATE CRYSTAL, AND ITS PREPARATION METHOD AND APPLICATION

CROSS-REFERENCE TO RELATED APPLICATIONS

This application claims the benefit of priority from Chinese Patent Application No. 202410881394.X, filed on Jul. 3, 2024. The content of the aforementioned application, including any intervening amendments made thereto, is incorporated herein by reference in its entirety.

TECHNICAL FIELD

This application relates to biomedicine technologies, and more particularly to a nicotinamide riboside hydrogen malate crystal, and its preparation method and application.

BACKGROUND

Nicotinamide riboside demonstrates an activity in enhancing nicotinamide adenine dinucleotide (NAD) levels in tissues, improving insulin sensitivity and activating the sirtuin function. Its ability to increase the NAD level further suggests that nicotinamide riboside can also improve mitochondrial health, stimulate mitochondrial function and trigger the generation of fresh mitochondria. It has been proved by researches associated with the use of nicotinamide riboside in Alzheimer's disease models that the nicotinamide riboside has an excellent brain bioavailability and can offer a remarkable neuroprotective effect through stimulating the NAD synthesis in the brain. Moreover, it has also been reported that dietary supplementation with nicotinamide riboside can inhibit liver cancer progression and induce tumor regression in mice, without any adverse effects even at high doses.

Currently, the commercially-available nicotinamide riboside products are dominated by nicotinamide riboside chloride (3-carbamoyl-1-[(2R,3R,4S,5R)-3,4-dihydroxy-5-hydroxymethyl-tetrahydrofuran-2-yl]pyridinium chloride, also known as 1-(β-D-ribofuranosyl)nicotinamide chloride), represented by:

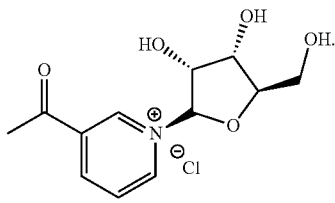

Nicotinamide riboside chloride is highly sensitive to light, air and humidity, and is thus extremely prone to degradation. Once degraded, its bioactivity will disappear. Therefore, it is important to develop a more structurally-stable nicotinamide riboside.

Nicotinamide riboside hydrogen malate is an existence form of nicotinamide riboside, and exhibits higher stability compared to nicotinamide riboside chloride. However, the nicotinamide riboside hydrogen malate crystal is significantly influenced by factors such as preparation process, crystallization control and crystallization solvent. Different preparation methods will yield distinct crystal forms, varying significantly in product stability and hygroscopicity. Existing nicotinamide riboside hydrogen malate crystals exhibit strong hygroscopicity and are prone to decomposition when exposed to air (higher temperatures will accelerate the degradation). For example, Chinese patent publication NO. 111454311A discloses a nicotinamide riboside hydrogen malate that must be prepared and filtered under oxygen-free, dry and low-temperature (below 0 C°) conditions.

SUMMARY

An object of the present disclosure is to provide a nicotinamide riboside hydrogen malate crystal to overcome the defects in the prior art. The nicotinamide riboside hydrogen malate crystal provided herein exhibits low hygroscopicity and higher thermal stability, maintaining good chemical stability even under the exposure to air, with minimal color change and preservation of solid form. A method for preparing the nicotinamide riboside hydrogen malate crystal is also provided. The nicotinamide riboside malate hydrogen crystal disclosed herein belongs to nicotinamide riboside products, and thus can be used as a drug for increasing the nicotinamide adenine dinucleotide (NAD) level in tissues, inducing insulin sensitivity and enhancing deacetylase (e.g., sirtuin) activity.

Technical solutions of the present disclosure are described as follows.

In a first aspect, this application provides a nicotinamide riboside hydrogen malate crystal, wherein the nicotinamide riboside hydrogen malate crystal has characteristic peaks respectively at 2θ values of 3.1703±0.2, 6.6434±0.2, 12.5953±0.2, 14.7209±0.2, 15.8502±0.2, 16.5144±0.2, 17.0509±0.2, 17.7053±0.2, 18.6569±0.2, 18.9470±0.2, 19.7757±0.2, 21.4535±0.2, 21.9161±0.2, 22.3721±0.2, 22.9562±0.2, 24.0469±0.2, 24.8641±0.2, 25.2183±0.2, 25.7679±0.2, 27.2584±0.2, 28.5494±0.2, 36.5968±0.2 and 36.8355±0.2.

In some embodiments, information of the characteristic peaks of the nicotinamide riboside hydrogen malate crystal (obtained by an X-ray powder diffraction method, with a 2θ value error range of ±0.2°) listed in the following table:

| Position (2θ) | Peak height (cts) | Interplanar spacing (Å) | Relative intensity (%) |
| --- | --- | --- | --- |
| 3.1703 | 116.16 | 27.86977 | 2.17 |
| 6.6434 | 1152.37 | 13.30537 | 21.57 |
| 11.6832 | 370.66 | 7.57462 | 6.94 |
| 12.5953 | 1921.68 | 7.02810 | 35.98 |
| 13.2216 | 307.88 | 6.69658 | 5.76 |
| 13.5116 | 285.92 | 6.55347 | 5.35 |
| 14.7209 | 650.41 | 6.01774 | 12.18 |
| 15.8502 | 606.61 | 5.59143 | 11.36 |
| 16.5144 | 2727.62 | 5.36801 | 51.06 |
| 17.0509 | 1261.49 | 5.20031 | 23.62 |
| 17.7053 | 1649.79 | 5.00953 | 30.89 |
| 18.6569 | 676.87 | 4.75613 | 12.67 |
| 18.9470 | 664.83 | 4.68395 | 12.45 |
| 19.7757 | 2119.86 | 4.48950 | 39.69 |
| 20.7033 | 184.48 | 4.29039 | 3.45 |
| 21.4535 | 5341.55 | 4.14202 | 100.00 |
| 21.9161 | 780.69 | 4.05563 | 14.62 |
| 22.3721 | 2301.43 | 3.97399 | 43.09 |
| 22.9562 | 1006.12 | 3.87419 | 18.84 |
| 24.0469 | 3241.71 | 3.70088 | 60.69 |
| 24.8641 | 1101.52 | 3.58107 | 20.62 |
| 25.2183 | 841.85 | 3.53156 | 15.76 |
| 25.7679 | 2952.04 | 3.45747 | 55.27 |
| 26.5234 | 448.56 | 3.36068 | 8.40 |

-continued

| Position (2θ) | Peak height (cts) | Interplanar spacing (Å) | Relative intensity (%) |
|---|---|---|---|
| 27.2584 | 1800.67 | 3.27171 | 33.71 |
| 27.7591 | 157.47 | 3.21383 | 2.95 |
| 28.5494 | 1725.78 | 3.12663 | 32.31 |
| 29.4106 | 448.40 | 3.03701 | 8.39 |
| 30.2726 | 223.20 | 2.95247 | 4.18 |
| 31.0188 | 459.00 | 2.88313 | 8.59 |
| 31.9060 | 328.96 | 2.80495 | 6.16 |
| 32.5552 | 174.63 | 2.75048 | 3.27 |
| 33.1237 | 100.31 | 2.70456 | 1.88 |
| 33.8682 | 387.80 | 2.64680 | 7.26 |
| 34.3609 | 458.74 | 2.60997 | 8.59 |
| 34.9700 | 150.08 | 2.56589 | 2.81 |
| 35.8684 | 76.39 | 2.50366 | 1.43 |
| 36.5968 | 1015.29 | 2.45548 | 19.01 |
| 36.8355 | 902.52 | 2.44011 | 16.90 |
| 38.3351 | 222.03 | 2.34804 | 4.16 |
| 39.3627 | 120.51 | 2.28908 | 2.26 |
| 39.9011 | 60.23 | 2.25943 | 1.13 |
| 40.2155 | 120.65 | 2.24249 | 2.26 |
| 41.1768 | 143.22 | 2.19233 | 2.68 |
| 42.3065 | 52.28 | 2.13637 | 0.98 |
| 42.9066 | 114.21 | 2.10787 | 2.14 |
| 44.9743 | 81.79 | 2.01565 | 1.53 |
| 46.5466 | 116.22 | 1.95116 | 2.18 |
| 47.7622 | 85.45 | 1.90430 | 1.60 |
| 48.6639 | 114.61 | 1.87110 | 2.15 |
| 49.4283 | 140.82 | 1.84394 | 2.64 |
| 51.6893 | 70.90 | 1.76848 | 1.33 |
| 52.8001 | 48.75 | 1.73386 | 0.91 |
| 56.1356 | 28.60 | 1.63849 | 0.54 |
| 57.2794 | 28.98 | 1.60846 | 0.54 |

In some embodiments, the nicotinamide riboside hydrogen malate crystal is prepared through steps of:
(1) mixing DL-malic acid with a solvent under stirring until the DL-malic acid is completely dissolved, so as to obtain a malic acid solution;
(2) adding a nicotinamide riboside chloride and a base to the malic acid solution followed by reaction;
(3) subjecting a reaction product to cooling and constant-temperature crystallization to obtain a crude product; and
(4) subjecting the crude product to filtration and drying to obtain the nicotinamide riboside hydrogen malate crystal in a form of white solid powder;
wherein in step (1), the solvent is selected from the group consisting of methanol, ethanol, N,N-dimethylformamide (DMF), acetone, dimethyl sulfoxide (DMSO), ethyl acetate, dichloromethane and 1,2-dichloroethane; the base is selected from the group consisting of ammonia water, sodium hydroxide, sodium carbonate, potassium carbonate, triethylamine (TEA), 1,2-diethylamine and N,N-diisopropylethylamine (DIEA); and in step (2), the reaction is carried out at 0-60° C.

In some embodiments, in step (2), the reaction is carried out at 40-60° C. for 1-3 h; in step (3), the constant-temperature crystallization is carried out at 0-10° C. for 1-3 h; and in step (4), the drying is carried out under reduced pressure at a vacuum degree of 500 Pa and a temperature of 30-60° C.

In some embodiments, a molar ratio of the DL-malic acid to the nicotinamide riboside chloride is 1:1.

In some embodiments, the base is DIEA.

Compared to the prior art, the present disclosure has the following beneficial effects.

Compared to commercially-available products, the nicotinamide riboside hydrogen malate crystal provided herein exhibits distinct characteristic peaks, superior air stability, thermal stability, low hygroscopicity and resistance to decomposition.

DETAILED DESCRIPTION OF EMBODIMENTS

To clarify the objects, technical solutions and beneficial effects of the present disclosure, the technical solutions of the present disclosure will be described in further detail below. It is obvious that described herein are merely some embodiments of the present disclosure, instead of all embodiments. Based on the embodiments in the present disclosure, all other embodiments obtained by those of ordinary skill in the art without making creative effort shall fall within the scope of the present disclosure defined by the appended claims.

To further clarify the present disclosure, the following detailed description is provided through the embodiments.

Example 1

200 mL of anhydrous methanol (unless otherwise specified, all solvents used were anhydrous), 48.43 g of DL-malic acid and 10 g of N,N-diisopropylethylamine (DIEA) were sequentially added to a three-neck flask under stirring until the DL-malic acid and DIEA were completely dissolved, followed by addition of nicotinamide riboside chloride, with a molar ratio of the nicotinamide riboside chloride to the DL-malic acid of 1:1. The reaction mixture was reacted at 40° C. and maintained at 40° C. under stirring for 2 h, then cooled naturally to 25° C. under stirring and held for 1 h, and then further cooled to 5° C. and held for 2 h.

The reaction process was as follows:

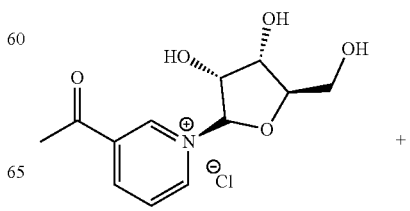

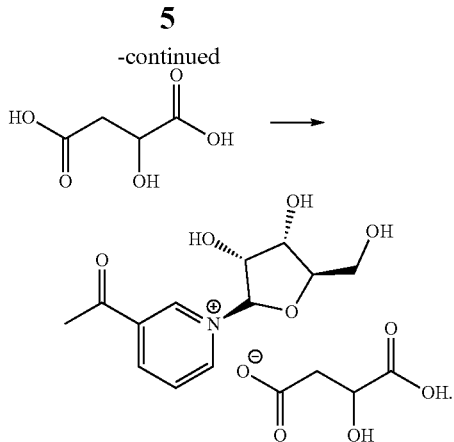

Figure 1:
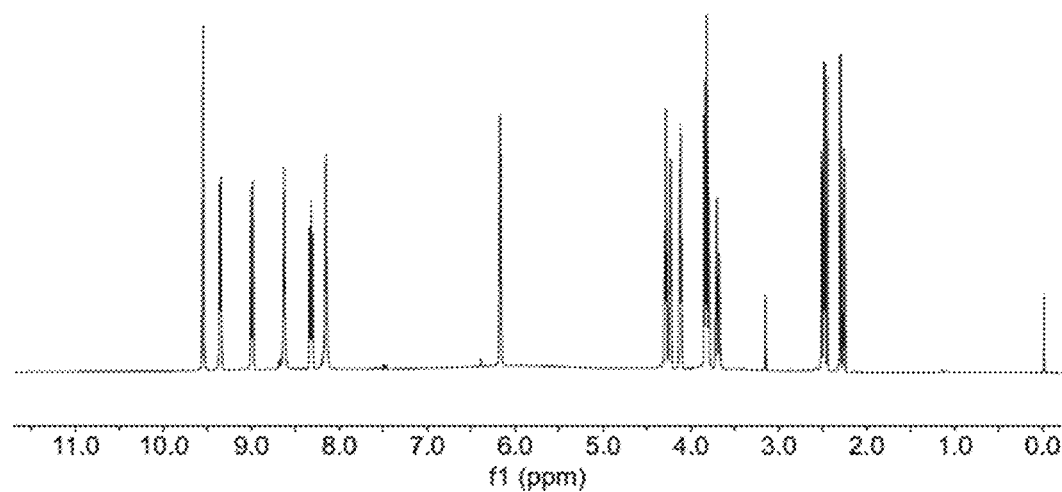
FIG. 1 is a proton nuclear magnetic resonance (1H NMR) spectrum of a nicotinamide riboside hydrogen malate crystal prepared in Example 1 of the present disclosure.

After holding for 2 h, the reaction mixture was subjected to filtration to obtain a filter residue. The filter residue was dried under reduced pressure at 50° C. overnight to yield a nicotinamide riboside hydrogen malate crystal in a form of white solid powder. Proton nuclear magnetic resonance ($^1$H-NMR) was performed to identify the white solid powder as the nicotinamide riboside hydrogen malate crystal (as shown in FIG. 1).

Nuclear magnetic resonance ($^1$H-NMR) characterization data were as follows. $^1$H-NMR (400 MHz, MeOD): γ 9.72 (s, 1H), 9.42-9.44 (d, 1H), 9.02-9.04 (d, 1H), 8.25-8.29 (t, 1H), 6.18-6.19 (d, 1H), 4.41-4.44 (m, 2H), 4.26-4.30 (m, 2H), 3.99-4.03 (dd, 1H), 3.83-3.87 (dd, 1H), 2.49-2.80 (dd, 2H).

The nicotinamide riboside hydrogen malate crystal obtained herein was analyzed as follows.

(1) X-Ray Powder Diffraction (XRPD) Analysis

Figure 2:
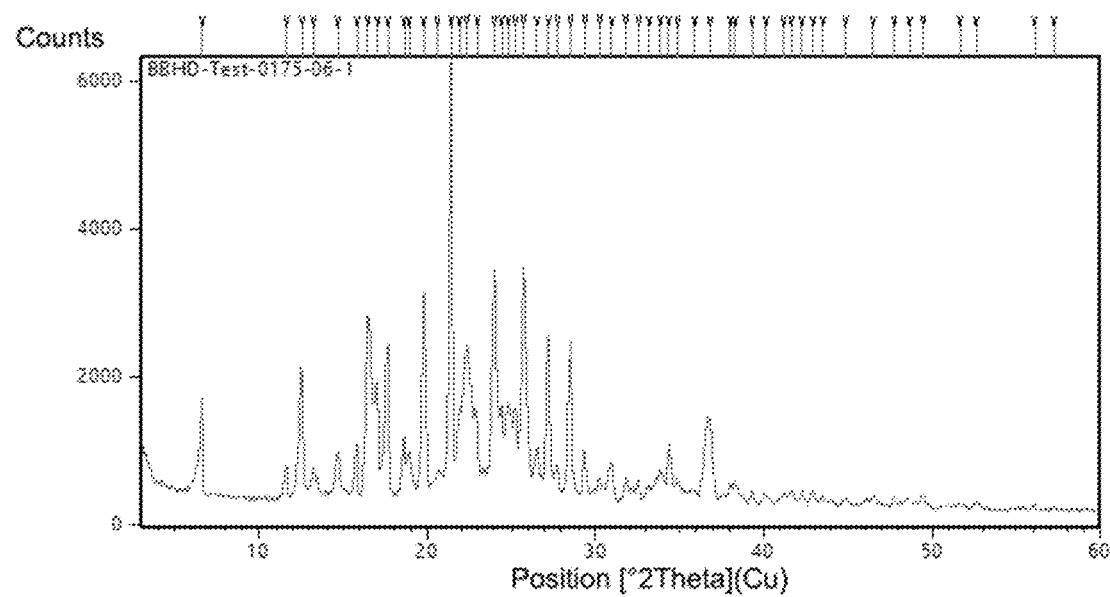
FIG. 2 is an X-ray diffraction (XRD) pattern of the nicotinamide riboside hydrogen malate crystal prepared in Example 1 of the present disclosure.

The XRPD analysis results were shown in Table 1 and FIG. 2.

TABLE 1

XRPD data of the nicotinamide riboside hydrogen malate crystal

| Position (°2θ) | Peak height (cts) | Interplanar spacing (Å) | Relative intensity (%) |
|---|---|---|---|
| 3.1703 | 116.16 | 27.86977 | 2.17 |
| 6.6434 | 1152.37 | 13.30537 | 21.57 |
| 11.6832 | 370.66 | 7.57462 | 6.94 |
| 12.5953 | 1921.68 | 7.02810 | 35.98 |
| 13.2216 | 307.88 | 6.69658 | 5.76 |
| 13.5116 | 285.92 | 6.55347 | 5.35 |
| 14.7209 | 650.41 | 6.01774 | 12.18 |
| 15.8502 | 606.61 | 5.59143 | 11.36 |
| 16.5144 | 2727.62 | 5.36801 | 51.06 |
| 17.0509 | 1261.49 | 5.20031 | 23.62 |
| 17.7053 | 1649.79 | 5.00953 | 30.89 |
| 18.6569 | 676.87 | 4.75613 | 12.67 |
| 18.9470 | 664.83 | 4.68395 | 12.45 |
| 19.7757 | 2119.86 | 4.48950 | 39.69 |
| 20.7033 | 184.48 | 4.29039 | 3.45 |
| 21.4535 | 5341.55 | 4.14202 | 100.00 |
| 21.9161 | 780.69 | 4.05563 | 14.62 |
| 22.3721 | 2301.43 | 3.97399 | 43.09 |
| 22.9562 | 1006.12 | 3.87419 | 18.84 |
| 24.0469 | 3241.71 | 3.70088 | 60.69 |
| 24.8641 | 1101.52 | 3.58107 | 20.62 |
| 25.2183 | 841.85 | 3.53156 | 15.76 |
| 25.7679 | 2952.04 | 3.45747 | 55.27 |
| 26.5234 | 448.56 | 3.36068 | 8.40 |
| 27.2584 | 1800.67 | 3.27171 | 33.71 |
| 27.7591 | 157.47 | 3.21383 | 2.95 |
| 28.5494 | 1725.78 | 3.12663 | 32.31 |
| 29.4106 | 448.40 | 3.03701 | 8.39 |
| 30.2726 | 223.20 | 2.95247 | 4.18 |
| 31.0188 | 459.00 | 2.88313 | 8.59 |
| 31.9060 | 328.96 | 2.80495 | 6.16 |
| 32.5552 | 174.63 | 2.75048 | 3.27 |
| 33.1237 | 100.31 | 2.70456 | 1.88 |
| 33.8682 | 387.80 | 2.64680 | 7.26 |
| 34.3609 | 458.74 | 2.60997 | 8.59 |
| 34.9700 | 150.08 | 2.56589 | 2.81 |
| 35.8684 | 76.39 | 2.50366 | 1.43 |
| 36.5968 | 1015.29 | 2.45548 | 19.01 |
| 36.8355 | 902.52 | 2.44011 | 16.90 |
| 38.3351 | 222.03 | 2.34804 | 4.16 |
| 39.3627 | 120.51 | 2.28908 | 2.26 |
| 39.9011 | 60.23 | 2.25943 | 1.13 |
| 40.2155 | 120.65 | 2.24249 | 2.26 |
| 41.1768 | 143.22 | 2.19233 | 2.68 |
| 42.3065 | 52.28 | 2.13637 | 0.98 |
| 42.9066 | 114.21 | 2.10787 | 2.14 |
| 44.9743 | 81.79 | 2.01565 | 1.53 |
| 46.5466 | 116.22 | 1.95116 | 2.18 |
| 47.7622 | 85.45 | 1.90430 | 1.60 |
| 48.6639 | 114.61 | 1.87110 | 2.15 |
| 49.4283 | 140.82 | 1.84394 | 2.64 |
| 51.6893 | 70.90 | 1.76848 | 1.33 |
| 52.8001 | 48.75 | 1.73386 | 0.91 |
| 56.1356 | 28.60 | 1.63849 | 0.54 |
| 57.2794 | 28.98 | 1.60846 | 0.54 |

(2) Thermogravimetric Analysis (TGA)

Figure 3:
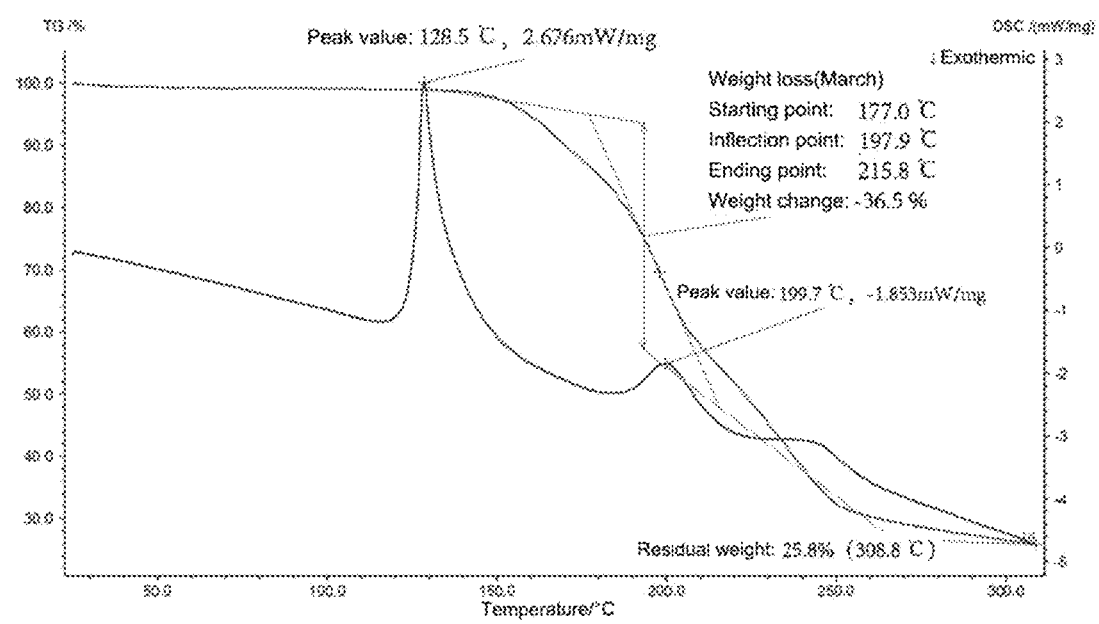
FIG. 3 is a thermogravimetric analysis (TGA) diagram of the nicotinamide riboside hydrogen malate crystal prepared in Example 1 of the present disclosure.

As shown in FIG. 3, the nicotinamide riboside hydrogen malate crystal exhibited a weight loss of 1-33% at 112-200° C.

(3) Differential Scanning Calorimetry (DSC) Analysis

Figure 4:
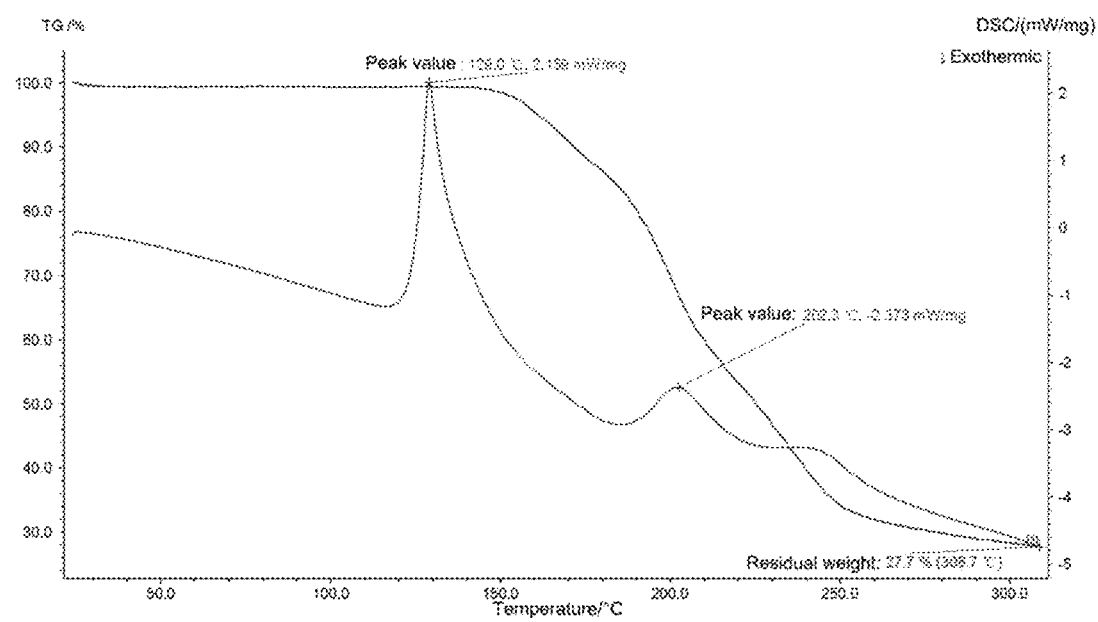
FIG. 4 is a differential scanning calorimetry (DSC) diagram of the nicotinamide riboside hydrogen malate crystal prepared in Example 1 of the present disclosure.

As shown in FIG. 4, the nicotinamide riboside hydrogen malate crystal exhibited an endothermic peak at 100-150° C.

(4) Infrared Spectroscopy (IR) Analysis

Figure 5:
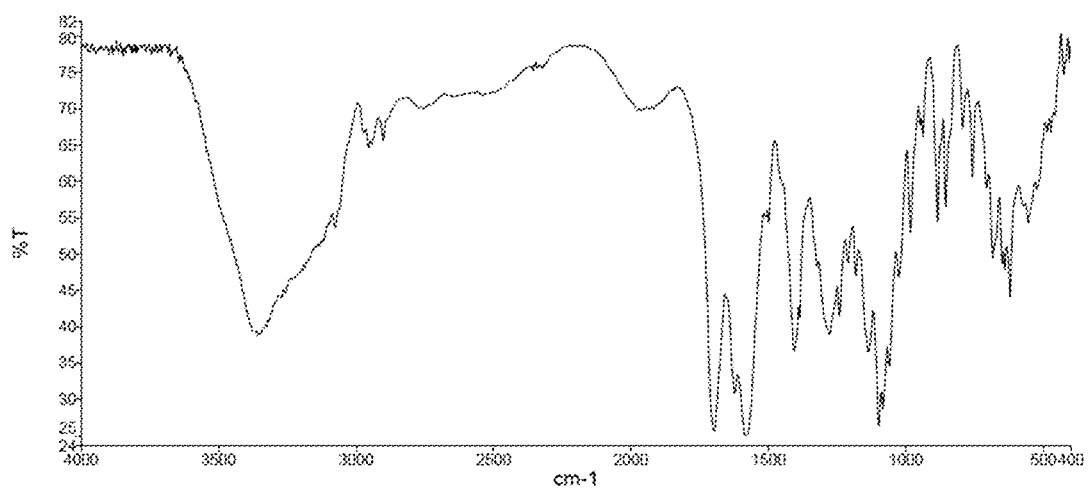
FIG. 5 is an infrared spectroscopy (IR) spectrum of the nicotinamide riboside hydrogen malate crystal prepared in Example 1 of the present disclosure.

As shown in FIG. 5, the IR spectrum (using a KBr pellet method) exhibited absorption peaks at $v_{max}$ values of 3360.30, 2955.76, 1697.79, 1582.55, 1082.63 and 619.05 cm$^{-1}$.

(5) Mass Spectrometry (MS) Analysis

Figure 6:
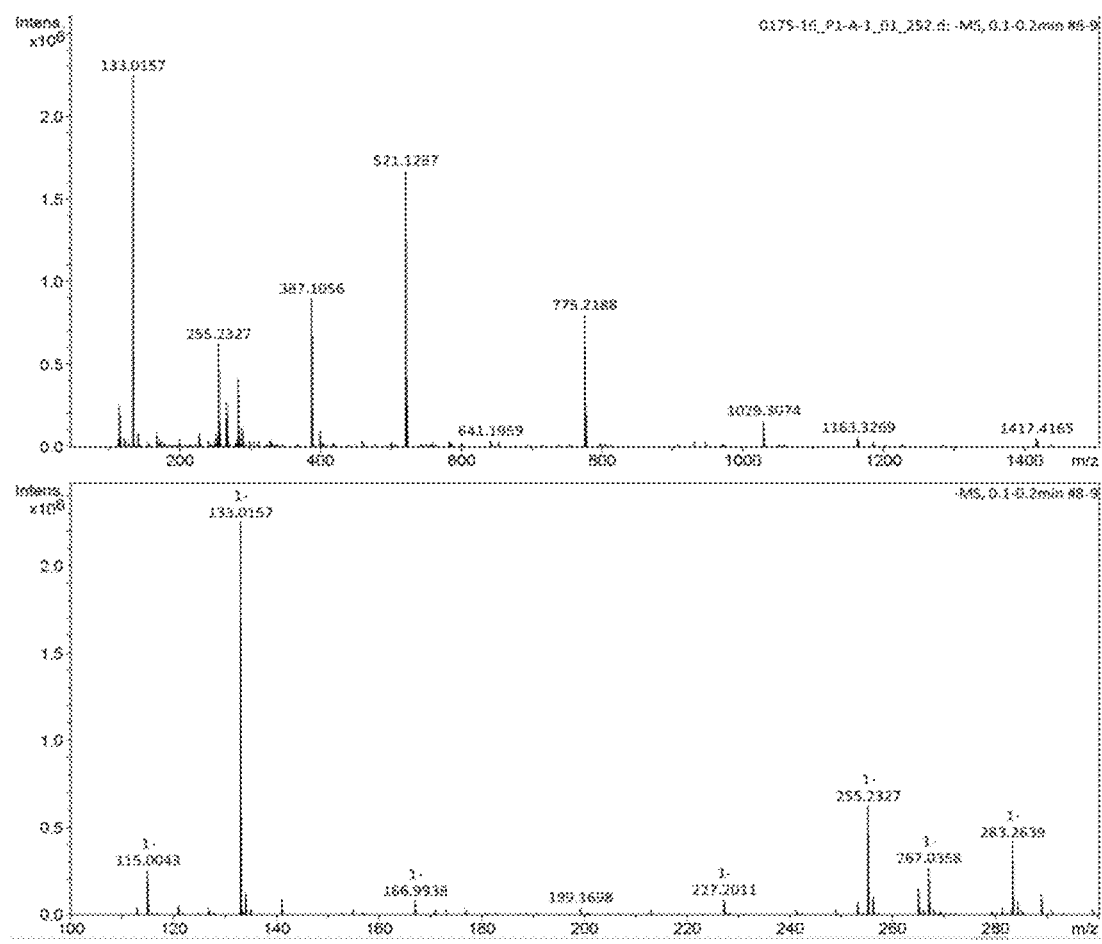
FIG. 6 is a mass spectrometry (MS) spectrum of the nicotinamide riboside hydrogen malate crystal prepared in Example 1 of the present disclosure.

As shown in FIG. 6, for the MS (ESI+) analysis, peaks were observed at m/z values of 255.10 [M+1] and 133.05 [M+1].

(6) Crystal Form Comparison

Figure 7:
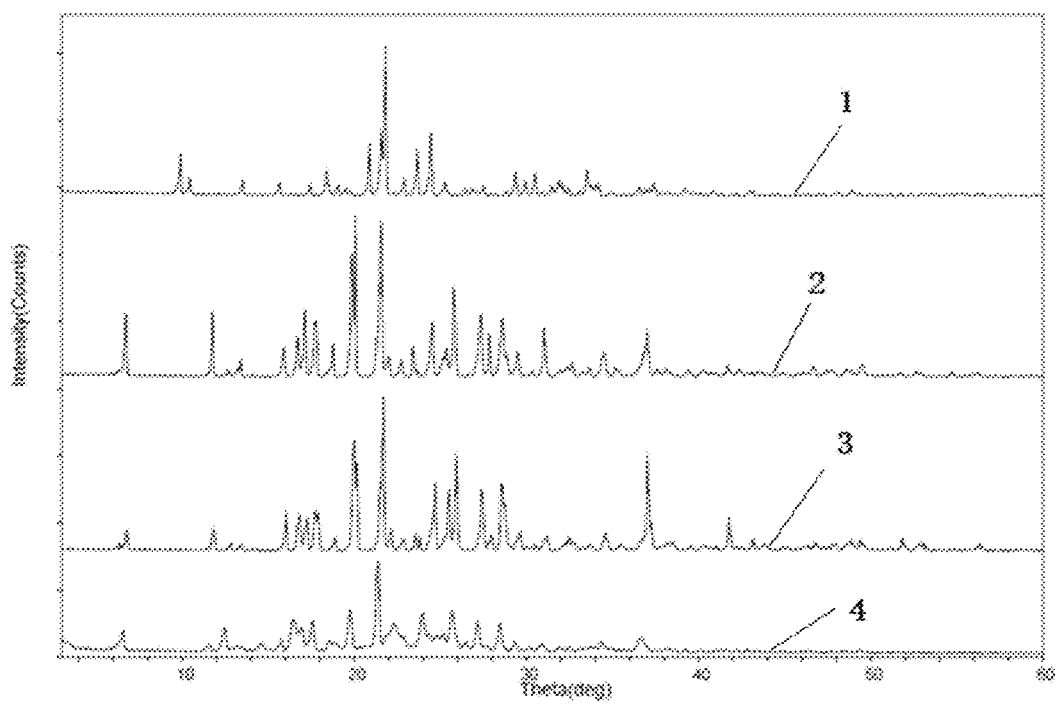
FIG. 7 is an X-ray powder diffraction (XRPD) comparison of the nicotinamide riboside hydrogen malate crystal prepared in Example 1 of the present disclosure and that of a commercially-available product.

The nicotinamide riboside hydrogen malate crystal provided herein was compared with three commercially-available nicotinamide riboside hydrogen malate crystal samples (labeled as sample A, sample B and sample C) by XRPD. The comparison results were shown in FIG. 7. Line 1 represented an XRPD pattern of the sample C, line 2 represented an XRPD pattern of the sample B, line 3 represented an XRPD pattern of the sample A and line 4 represented an XRPD pattern of the nicotinamide riboside hydrogen malate crystal prepared in Example 1 of the present disclosure. It can be seen from the comparison that the nicotinamide riboside hydrogen malate crystal obtained herein had characteristic peaks respectively at 2θ values of 3.1703±0.2, 6.6434±0.2, 12.5953±0.2, 14.7209±0.2, 15.8502±0.2, 16.5144±0.2, 17.0509±0.2, 17.7053±0.2, 18.6569±0.2, 18.9470±0.2, 19.7757±0.2, 21.4535±0.2, 21.9161±0.2, 22.3721±0.2, 22.9562±0.2, 24.0469±0.2, 24.8641±0.2, 25.2183±0.2, 25.7679±0.2, 27.2584±0.2, 28.5494±0.2, 36.5968±0.2, and 36.8355±0.2. These results indicated that the nicotinamide riboside hydrogen malate crystal of the present disclosure was a novel crystal.

(7) Stability Comparison

The nicotinamide riboside hydrogen malate crystal obtained herein and the commercially-available nicotinamide riboside hydrogen malate crystal samples (A and B) were each divided into seven portions and separately placed into seven glass sample dishes, with 1 g of sample in each dish. The dishes were covered and sealed. All the samples were stored in a constant-temperature-humidity chamber at 25° C. and a relative humidity of 40%. The purity of the samples was tested daily. The purity and decomposition rates over six days were shown in Table 3. The decomposition rate was calculated using the following formula: decomposition rate=(initial sample purity−sample purity)/initial sample purity×100%.

Product purity analysis was performed through the following steps. One packet of the sample was dissolved in a 5 mL or 10 mL volumetric flask to prepare a 5 mL or 10 mL sample solution. Then, the purity of the sample was determined using high performance liquid chromatography (HPLC).

TABLE 2

Comparison of purity and decomposition rate between nicotinamide riboside hydrogen malate crystal obtained herein and commercially-available products

| Time (day) | Product of Example 1 | Commercially-available product A | Commercially-available product B |
| --- | --- | --- | --- |
| 0 | 99.576% | 99.900% | 99.750% |
| 1 | 99.553% | 98.355% | 98.843% |
| 2 | 99.494% | 96.843% | 98.310% |
| 3 | 99.510% | 95.752% | 97.982% |
| 4 | 99.518% | 94.185% | 96.530% |
| 5 | 99.499% | 93.250% | 95.020% |
| 6 | 98.820% | 91.538% | 94.989% |
| Decomposition rate over 6 days | 0.759% | 8.37% | 4.77% |

As shown in Table 2, the nicotinamide riboside hydrogen malate crystal provided herein exhibited better stability compared to the commercially-available products.

Comparative Example 1

Without Adding Alkali 200 mL of anhydrous methanol and 48.43 g of DL-malic acid were added to a three-necked flask under stirring until the DL-malic acid was completely dissolved, followed by addition of nicotinamide riboside chloride, with a molar ratio of the nicotinamide riboside chloride to the DL-malic acid of 1:1. The reaction mixture was reacted at 40° C. and maintained at 40° C. under stirring for 2 h, then cooled to 25° C. under stirring and held for 1 h, and then further cooled to 5° C. and kept for 2 h, no crystalline product was obtained.

The essence of the present disclosure was to use the nicotinamide riboside chloride as a substrate and replace the chloride ion with the malate anion. However, under a non-alkaline condition, the reaction could not proceed and nicotinamide riboside hydrogen malate crystal could not be obtained.

Comparative Example 2

Adjusting the Order of Addition of DL-Malic Acid and Nicotinamide Riboside Chloride 200 mL of anhydrous methanol, the nicotinamide riboside chloride and 10 g of N,N-diisopropylethylamine (DIEA) were sequentially added to a three-necked flask under stirring until DIEA was completely dissolved, followed by addition of 48.43 g of DL-malic acid, with a molar ratio of the nicotinamide riboside chloride to the DL-malic acid of 1:1. The reaction mixture was reacted at 40° C. and maintained at 40° C. under stirring for 2 h, then cooled to 25° C. under stirring and held for 1 h, and then cooled to 5° C. and maintained for 2 h, resulting in a white turbid reaction mixture. The white turbid reaction mixture was subjected to centrifugation and filtration to yield the desired nicotinamide riboside hydrogen malate crystal.

If the nicotinamide riboside chloride and DIEA were mixed first without the presence of the DL-malic acid, prolonged stirring time would lead to significant decomposition of the nicotinamide riboside chloride, greatly reducing the product yield.

Example 2

660 L of ethanol, 145.29 kg of DL-malic acid and nicotinamide riboside chloride were sequentially added to a three-necked flask under stirring until the DL-malic acid was completely dissolved, followed by addition of 30 kg of N,N-diisopropylethylamine (DIEA), with a molar ratio of the nicotinamide riboside chloride to the DL-malic acid of 1:1. The reaction mixture was reacted at 40° C. and maintained at 40° C. under stirring for 2 h, then cooled to 25° C. under stirring and held for 1 h, and then cooled to 5° C. and maintained for 2 h, resulting in a white, turbid and viscous reaction mixture. Then, the reaction mixture was subjected to centrifugation, filtration and drying under reduced pressure overnight at 50° C. to yield a white solid powder. The solid powder was confirmed as the nicotinamide riboside hydrogen malate crystal by proton nuclear magnetic resonance ($^1$H NMR).

Example 3

100 mL of isopropanol, 24 g of DL-malic acid and 5.2 g of N,N-diisopropylethylamine (DIEA) were sequentially added to a three-necked flask under stirring until the DL-malic acid and DIEA were completely dissolved, followed by addition of nicotinamide riboside chloride, with a molar ratio of the nicotinamide riboside chloride to the DL-malic acid of 1:1. The reaction mixture was reacted at 40° C. and maintained at 40° C. under stirring for 2 h, then cooled to 25° C. under stirring and held for 1 h, and then cooled to 5° C. and maintained for 2 h. Then, the resulting mixture was subjected to filtration and drying under reduced pressure overnight at 50° C. to yield a white solid powder. The solid powder was confirmed as the nicotinamide riboside hydrogen malate crystal by proton nuclear magnetic resonance ($^1$H NMR).

Example 4

500 mL of 1,4-dioxane, 121 g of DL-malic acid and 25 g of N,N-diisopropylethylamine (DIEA) were sequentially added to a three-necked flask under stirring until the DL-malic acid and DIEA were completely dissolved, followed by addition of nicotinamide riboside chloride, with a molar ratio of the nicotinamide riboside chloride to the DL-malic acid of 1:1. The reaction mixture was reacted at 40° C. and maintained at 40° C. under stirring for 2 h, then cooled to 25° C. under stirring and held for 1 h, and then cooled to 5°

C. and maintained for 2 h. The resulting mixture was subjected to filtration and drying under reduced pressure overnight at 50° C. to yield a white solid powder. The solid powder was confirmed as the nicotinamide riboside hydrogen malate crystal by proton nuclear magnetic resonance ($^1$H NMR).

Example 5

1000 mL of tetrahydrofuran, 242 g of DL-malic acid and 50 g of N,N-diisopropylethylamine (DIEA) were sequentially added to a three-necked flask under stirring until the DL-malic acid and DIEA were completely dissolved, followed by addition of nicotinamide riboside chloride, with a molar ratio of the nicotinamide riboside chloride to the DL-malic acid of 1:1. The reaction mixture was reacted at 40° C. and maintained at 40° C. under stirring for 2 h, then cooled to 25° C. under stirring and held for 1 h, and then cooled to 5° C. and maintained for 2 h. Then, the resulting mixture was subjected to filtration and drying under reduced pressure overnight at 50° C. to yield a white solid powder. The solid powder was confirmed as the nicotinamide riboside hydrogen malate crystal by proton nuclear magnetic resonance ($^1$H NMR).

Example 6

3000 mL of acetonitrile, 300 g of DL-malic acid and 62 g of N,N-diisopropylethylamine (DIEA) were sequentially added to a three-necked flask under stirring until the DL-malic acid and DIEA were completely dissolved, followed by addition of nicotinamide riboside chloride, with a molar ratio of the nicotinamide riboside chloride to the DL-malic acid of 1:1. The reaction mixture was reacted at 40° C. and maintained at 40° C. under stirring for 2 h, then cooled to 25° C. under stirring and held for 1 h, and then cooled to 5° C. and maintained for 2 h. Then, the resulting mixture was subjected to filtration and drying under reduced pressure overnight at 50° C. to yield a white solid powder. The solid powder was confirmed as the nicotinamide riboside hydrogen malate crystal by proton nuclear magnetic resonance ($^1$H NMR).

Quality analysis of each Example and Comparative Examples products (1) Stability Comparison The nicotinamide riboside hydrogen malate crystal obtained from the above Examples and Comparative Examples products was sealed in polyethylene (PE) bags, with 1 gram per bag. The bags were then stored in a constant-temperature-humidity chamber at 25° C. and a relative humidity of 40%. Samples were tested at regular intervals.

Sample solution was prepared through the following steps. For each test, a bag of sample was dissolved in a 5 mL or 10 mL volumetric flask to obtain a 5 mL or 10 mL sample solution. Then, the sample solution was filtered through a membrane, and the sample purity was determined using high performance liquid chromatography (HPLC). The product purity and decomposition rate data on day 6 were shown in Table 3. The decomposition rate was calculated using the following formula: decomposition rate=(initial sample purity−sample purity)/initial sample purity×100%.

TABLE 3

Changes in product purity and decomposition rate (25° C., RH 40%)

| Item | Initial purity (%) | Purity on day 6 (%) | Decomposition rate on day 6 (%) |
|---|---|---|---|
| EXAMPLE 1 | 99.67 | 99.65 | 0.72 |
| EXAMPLE 2 | 99.72 | 98.97 | 0.75 |
| EXAMPLE 3 | 99.69 | 98.95 | 0.74 |
| EXAMPLE 4 | 99.51 | 98.79 | 0.72 |
| EXAMPLE 5 | 99.78 | 99.15 | 0.63 |
| EXAMPLE 6 | 99.81 | 99.11 | 0.70 |

(2) Color Change and Hygroscopicity Rate Comparison

The nicotinamide riboside hydrogen malate crystal products obtained from the above Examples and Comparative Examples were respectively exposed to air (air humidity and temperature were controlled). The color changes of the products on day 0 and day 6 were observed, and moisture determination was performed. The observation and analysis results were shown in Table 4.

TABLE 4

Color and moisture changes of the products exposed to air (25° C., RH 40%)

| | Day 0 | | Day 6 | |
|---|---|---|---|---|
| Item | Product appearance | Product moisture (%) | Product appearance | Product moisture (%) |
| EXAMPLE 1 | White | 0.30 | White | 2 |
| EXAMPLE 2 | White | 0.28 | White | 3.1 |
| EXAMPLE 3 | White | 0.30 | White | 2.4 |
| EXAMPLE 4 | White | 0.22 | White | 1.8 |
| EXAMPLE 5 | White | 0.31 | White | 2.9 |
| EXAMPLE 6 | White | 0.29 | White | 3.2 |

The analysis method used herein involved X-ray powder diffraction (XRPD) method using a Bruker D2 Phaser X-ray powder diffractometer with a Cu radiation source (1.54184 Å), generator settings of 30 kV and 10 mA, an initial 2θ of 2.000°, a scanning range of 2.0000-50.000°, a step size of 0.02° and a scanning speed of 0.1 s/step.

Measurement discrepancies in X-ray powder diffraction analysis results were attributed to several factors, including errors in sample preparation (e.g., sample height), instrumental errors, calibration differences, operator errors (e.g., errors in determining peak positions) and material properties (e.g., preferred orientation errors). Calibration errors and sample height errors frequently caused all peaks to shift in the same direction. When a flat holder was used, small differences in sample height resulted in significant shifts in XRPD peak positions. Systematic studies demonstrated that 1 mm difference in sample height could lead to peak shifts of up to 1° in 2θ. These shifts were identifiable from XRPD patterns and could be corrected either by compensating for the shifts (e.g., applying a system calibration factor to all peak positions) or by recalibrating the instrument to eliminate the shifts. As described above, applying a system calibration factor to align peak positions can correct measurement errors from different instruments.

Thermogravimetric analysis (TGA) was performed using a TGA55 instrument from TA Instruments, USA, with a temperature range of 14.8-300° C., a heating rate of 10° C./min and a nitrogen flow rate of 40 mL/min.

Differential scanning calorimetry (DSC) was performed using a TAQ55 instrument from TA Instruments, USA, with a temperature range of 20-230° C., a heating rate of 10° C./min and a nitrogen flow rate of 50 mL/min.

Moisture (Karl Fischer) determination method was performed using an MC-2000 automatic micro-moisture analyzer from Mince Instruments (Xiamen) Co., Ltd., and a karl fischer reagent from Nanjing Chemical Reagent Co., Ltd.

The high performance liquid chromatography (HPLC) method parameters were as follows: isocratic elution with 5% water (0.1% formic acid) and 95% methanol (0.1% formic acid) as the mobile phase, a wavelength of 254 nm, a temperature of 23.0° C. with 54% relative humidity, samples dissolved in methanol, an ODS-2 column (4.6×250 mm, 5 m) with pressure maintained at 12-13 MPa, a flow rate of 1.0 mL/min, an injection volume of 5 L and a run time greater than or equal to 15 min.

The embodiments described above are merely illustrative of the present disclosure, and are not intended to limit the scope of the present disclosure. It should be understood that various changes or substitutions made by those of ordinary skill in the art without departing from the spirit of the present disclosure shall fall within the scope of the present disclosure defined by the appended claims.

What is claimed is:

1. A nicotinamide riboside hydrogen malate crystal, wherein the nicotinamide riboside hydrogen malate crystal has characteristic peaks respectively at 2θ values of 3.1703±0.2, 6.6434±0.2, 12.5953±0.2, 14.7209±0.2, 15.8502±0.2, 16.5144±0.2, 17.0509±0.2, 17.7053±0.2, 18.6569±0.2, 18.9470±0.2, 19.7757±0.2, 21.4535±0.2, 21.9161±0.2, 22.3721±0.2, 22.9562±0.2, 24.0469±0.2, 24.8641±0.2, 25.2183±0.2, 25.7679±0.2, 27.2584±0.2, 28.5494±0.2, 36.5968±0.2 and 36.8355±0.2; and
   the nicotinamide riboside hydrogen malate crystal is prepared through steps of:
   (1) mixing DL-malic acid with a solvent under stirring until the DL-malic acid is completely dissolved, so as to obtain a malic acid solution;
   (2) adding a nicotinamide riboside chloride and a base to the malic acid solution followed by reaction;
   (3) subjecting a reaction product to cooling and constant-temperature crystallization to obtain a crude product; and
   (4) subjecting the crude product to filtration and drying to obtain the nicotinamide riboside hydrogen malate crystal in a form of white solid powder;
   wherein in step (1), the solvent is selected from the group consisting of methanol, ethanol, N,N-dimethylformamide (DMF), acetone, dimethyl sulfoxide (DMSO), ethyl acetate, dichloromethane and 1,2-dichloroethane;
   the base is selected from the group consisting of ammonia water, sodium hydroxide, sodium carbonate, potassium carbonate, triethylamine (TEA), 1,2-diethylamine and N,N-diisopropylethylamine (DIEA); and
   in step (2), the reaction is carried out at 0-60° C.

2. The nicotinamide riboside hydrogen malate crystal of claim 1, wherein information of the characteristic peaks of the nicotinamide riboside hydrogen malate crystal is listed in the following table:

| Position (°2θ) | Peak height (cts) | Interplanar spacing (Å) | Relative intensity (%) |
| --- | --- | --- | --- |
| 3.1703 | 116.16 | 27.86977 | 2.17 |
| 6.6434 | 1152.37 | 13.30537 | 21.57 |
| 11.6832 | 370.66 | 7.57462 | 6.94 |
| 12.5953 | 1921.68 | 7.02810 | 35.98 |
| 13.2216 | 307.88 | 6.69658 | 5.76 |
| 13.5116 | 285.92 | 6.55347 | 5.35 |
| 14.7209 | 650.41 | 6.01774 | 12.18 |
| 15.8502 | 606.61 | 5.59143 | 11.36 |
| 16.5144 | 2727.62 | 5.36801 | 51.06 |
| 17.0509 | 1261.49 | 5.20031 | 23.62 |
| 17.7053 | 1649.79 | 5.00953 | 30.89 |
| 18.6569 | 676.87 | 4.75613 | 12.67 |
| 18.9470 | 664.83 | 4.68395 | 12.45 |
| 19.7757 | 2119.86 | 4.48950 | 39.69 |
| 20.7033 | 184.48 | 4.29039 | 3.45 |
| 21.4535 | 5341.55 | 4.14202 | 100.00 |
| 21.9161 | 780.69 | 4.05563 | 14.62 |
| 22.3721 | 2301.43 | 3.97399 | 43.09 |
| 22.9562 | 1006.12 | 3.87419 | 18.84 |
| 24.0469 | 3241.71 | 3.70088 | 60.69 |
| 24.8641 | 1101.52 | 3.58107 | 20.62 |
| 25.2183 | 841.85 | 3.53156 | 15.76 |
| 25.7679 | 2952.04 | 3.45747 | 55.27 |
| 26.5234 | 448.56 | 3.36068 | 8.40 |
| 27.2584 | 1800.67 | 3.27171 | 33.71 |
| 27.7591 | 157.47 | 3.21383 | 2.95 |
| 28.5494 | 1725.78 | 3.12663 | 32.31 |
| 29.4106 | 448.40 | 3.03701 | 8.39 |
| 30.2726 | 223.20 | 2.95247 | 4.18 |
| 31.0188 | 459.00 | 2.88313 | 8.59 |
| 31.9060 | 328.96 | 2.80495 | 6.16 |
| 32.5552 | 174.63 | 2.75048 | 3.27 |
| 33.1237 | 100.31 | 2.70456 | 1.88 |
| 33.8682 | 387.80 | 2.64680 | 7.26 |
| 34.3609 | 458.74 | 2.60997 | 8.59 |
| 34.9700 | 150.08 | 2.56589 | 2.81 |
| 35.8684 | 76.39 | 2.50366 | 1.43 |
| 36.5968 | 1015.29 | 2.45548 | 19.01 |
| 36.8355 | 902.52 | 2.44011 | 16.90 |
| 38.3351 | 222.03 | 2.34804 | 4.16 |
| 39.3627 | 120.51 | 2.28908 | 2.26 |
| 39.9011 | 60.23 | 2.25943 | 1.13 |
| 40.2155 | 120.65 | 2.24249 | 2.26 |
| 41.1768 | 143.22 | 2.19233 | 2.68 |
| 42.3065 | 52.28 | 2.13637 | 0.98 |
| 42.9066 | 114.21 | 2.10787 | 2.14 |
| 44.9743 | 81.79 | 2.01565 | 1.53 |
| 46.5466 | 116.22 | 1.95116 | 2.18 |
| 47.7622 | 85.45 | 1.90430 | 1.60 |
| 48.6639 | 114.61 | 1.87110 | 2.15 |
| 49.4283 | 140.82 | 1.84394 | 2.64 |
| 51.6893 | 70.90 | 1.76848 | 1.33 |
| 52.8001 | 48.75 | 1.73386 | 0.91 |
| 56.1356 | 28.60 | 1.63849 | 0.54 |
| 57.2794 | 28.98 | 1.60846 | 0.54. |

3. The nicotinamide riboside hydrogen malate crystal of claim 1, wherein in step (2), the reaction is carried out at 40-60° C. for 1-3 h;
   in step (3), the constant-temperature crystallization is carried out at 0-10° C. for 1-3 h; and
   in step (4), the drying is carried out under reduced pressure at a vacuum degree of 500 Pa and a temperature of 30-60° C.

4. The nicotinamide riboside hydrogen malate crystal of claim 3, wherein a molar ratio of the DL-malic acid to the nicotinamide riboside chloride is 1:1.

5. The nicotinamide riboside hydrogen malate crystal of claim 1, wherein the base is DIEA.

* * * * *